(12) United States Patent
Kim

(10) Patent No.: US 10,956,011 B2
(45) Date of Patent: Mar. 23, 2021

(54) METHOD AND DEVICE FOR OUTPUTTING PARAMETER INFORMATION FOR SCANNING FOR MAGNETIC RESONANCE IMAGES

(71) Applicant: SAMSUNG ELECTRONICS CO., LTD., Suwon-si (KR)

(72) Inventor: Joo-young Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 65 days.

(21) Appl. No.: 15/367,564

(22) Filed: Dec. 2, 2016

(65) Prior Publication Data

US 2017/0185280 A1    Jun. 29, 2017

(30) Foreign Application Priority Data

Dec. 28, 2015 (KR) .......................... 10-2015-0187631

(51) Int. Cl.
*G06F 3/0484*    (2013.01)
*G01R 33/54*    (2006.01)
(Continued)

(52) U.S. Cl.
CPC ....... *G06F 3/04847* (2013.01); *G01R 33/543* (2013.01); *G01R 33/546* (2013.01); *G16H 30/20* (2018.01); *G16H 40/63* (2018.01)

(58) Field of Classification Search
CPC .... G06F 3/04847; G16H 40/63; G16H 30/20; G01R 33/543; G01R 33/546
(Continued)

(56) References Cited

U.S. PATENT DOCUMENTS 5,615,347 A * 3/1997 Davis ................. G06F 3/04847
715/804
6,687,527 B1 * 2/2004 Wu ........................ G01R 33/546
324/318
(Continued)

FOREIGN PATENT DOCUMENTS

CN    103177738 A    6/2013
EP    2608076 A2    6/2013
(Continued)

OTHER PUBLICATIONS

Communication dated Jun. 1, 2017 by the Korean Intellectual Property Office in counterpart Korean Patent Application No. 10-2015-0187631.
(Continued)

*Primary Examiner* — David S Posigian
(74) *Attorney, Agent, or Firm* — Sughrue Mion, PLLC

(57) ABSTRACT

A method of outputting information about parameters for magnetic resonance imaging (MRI) includes receiving editing information that is used to change a value of a first parameter, outputting information representing a first range of the first parameter, based on the received editing information, the first range enabling a value of a second parameter that is associated with the first parameter to be changed together with the value of the first parameter, and outputting a value to which the second parameter is changeable, according to a value to which the first parameter is changeable, based on the received editing information.

9 Claims, 12 Drawing Sheets

(51) Int. Cl.
*G16H 30/20* (2018.01)
*G16H 40/63* (2018.01)

(58) Field of Classification Search
USPC .................................. 715/771, 833, 970, 974
See application file for complete search history.

(56) References Cited

U.S. PATENT DOCUMENTS

| | | | | |
|---|---|---|---|---|
| 6,850,254 | B1* | 2/2005 | Banning | G06F 3/04847 |
| | | | | 715/764 |
| 7,051,286 | B1* | 5/2006 | Stemmer | G16H 40/63 |
| | | | | 715/762 |
| 7,080,324 | B1* | 7/2006 | Nelson | G06F 3/04847 |
| | | | | 715/771 |
| 2003/0088173 | A1* | 5/2003 | Kassai | G01R 33/28 |
| | | | | 600/408 |
| 2003/0095144 | A1 | 5/2003 | Trevino et al. | |
| 2003/0095150 | A1* | 5/2003 | Trevino | G01R 33/546 |
| | | | | 715/810 |
| 2004/0267117 | A1 | 12/2004 | Wright et al. | |
| 2007/0098240 | A1* | 5/2007 | Takayama | G01R 33/54 |
| | | | | 382/128 |
| 2008/0104533 | A1* | 5/2008 | List | A61B 5/055 |
| | | | | 715/771 |
| 2008/0120565 | A1* | 5/2008 | Stiso | G06F 3/04847 |
| | | | | 715/771 |
| 2008/0126968 | A1* | 5/2008 | West | G16H 40/63 |
| | | | | 715/771 |
| 2008/0256489 | A1* | 10/2008 | Maurer | G06F 3/04847 |
| | | | | 715/833 |
| 2009/0175524 | A1* | 7/2009 | Kachi | G01R 33/54 |
| | | | | 382/131 |
| 2011/0021904 | A1 | 1/2011 | Burrman | |
| 2013/0091454 | A1* | 4/2013 | Papa | G06F 3/04847 |
| | | | | 715/772 |
| 2013/0097551 | A1* | 4/2013 | Hogan | G06F 3/0488 |
| | | | | 715/780 |
| 2013/0263046 | A1* | 10/2013 | Takahashi | G06F 3/0484 |
| | | | | 715/788 |
| 2013/0293570 | A1* | 11/2013 | Dolgos | A61M 1/16 |
| | | | | 345/619 |
| 2013/0338930 | A1 | 12/2013 | Senegas et al. | |
| 2014/0363062 | A1 | 12/2014 | Han | |
| 2015/0020016 | A1* | 1/2015 | Hanumara | G06F 3/04847 |
| | | | | 715/771 |
| 2016/0116557 | A1* | 4/2016 | Feiweier | G01R 33/543 |
| | | | | 324/309 |
| 2016/0231396 | A1 | 8/2016 | Sunaga et al. | |
| 2016/0283192 | A1 | 9/2016 | Friesen et al. | |

FOREIGN PATENT DOCUMENTS

| | | |
|---|---|---|
| JP | 8336504 A | 12/1996 |
| JP | 11-47109 A | 2/1999 |
| JP | 2006255189 A | 9/2006 |
| JP | 2008-176 A | 1/2008 |
| JP | 2011-120781 A | 6/2011 |
| JP | 2011200342 A | 10/2011 |
| JP | 20139762 A | 1/2013 |
| JP | 2015-54040 A | 3/2015 |
| WO | 2015/056569 A1 | 4/2015 |

OTHER PUBLICATIONS

Communication dated Jan. 17, 2017, issued by the Korean Intellectual Property Office in counterpart Korean Application No. 10-2015-0187631.
Communication dated Mar. 10, 2017, issued by the International Searching Authority in counterpart International Application No. PCT/KR2016/013779 (PCT/ISA/210 & PCT/ISA/237).
Communication dated Sep. 26, 2017, issued by the European Patent Office in counterpart European Patent Application No. 16204465.5.
Communication dated Apr. 17, 2018, issued by the European Patent Office in counterpart European Patent Application No. 16204465.5.
Communication dated Aug. 2, 2019, from the State Intellectual Property Office of People's Republic of China in counterpart Application No. 201611235458.0.
Communication dated Oct. 20, 2020, issued by the European Patent Office in counterpart European Application No. 16204465.5.

* cited by examiner

| Start Scan | Stop Scan | Skip | | | | | | |

| Summary | Common |
|---|---|

| Contrast | Number of Slice Groups | − | + | 1 | | 630 — TR | 4580.00 ms | ◄► |
| Resolution | Number of Slice | | | 8 | ◄► | 640 — TE | 99.80 ms | ◄► |
| Geometry | Slice Gap | | | 1.50mm | ◄► | Average | 3 | ◄► |
| Sequence | Position | | | isocenter | ▶ | Concatenations | 1 | ◄► |
| Recon | Orientation | | | Transversal | ▶ | Number of TXs | 2 | ◄► |
| Physio | Phase Encoding Direction | | | R>>L | ▶ | | | |
| System | Phase Oversampling | | | 0.00% | ◄► | | | |
| Respiration | 610 — FoV Read | | | 240 mm | ◄► | | | |
| Coil | 620 — FoV Phase | | | 187 mm | ◄► | | | |
| User | Slice Thickness | | | 5.00 | ◄► | | | |

METHOD AND DEVICE FOR OUTPUTTING PARAMETER INFORMATION FOR SCANNING FOR MAGNETIC RESONANCE IMAGES

CROSS-REFERENCE TO RELATED PATENT APPLICATION

This application claims priority from Korean Patent Application No. 10-2015-0187631, filed on Dec. 28, 2015, in the Korean Intellectual Property Office, the disclosure of which is incorporated herein by reference in its entirety.

BACKGROUND

1. Field

Methods and apparatuses consistent with exemplary embodiments relate to a method and an apparatus for editing a parameter for scanning for magnetic resonance images.

2. Description of the Related Art

Medical imaging apparatuses are used to acquire an internal structure of an object as an image. Medical imaging apparatuses are noninvasive examination apparatuses that scan a human body and process images of the structural details of the human body, internal tissue thereof, and fluid flow within a human body and provide the processed images to a user. A user, such as a doctor, may diagnose a health state and a disease of a patient by using a medical image output from a medical imaging apparatus.

Examples of the medical imaging apparatuses may include a magnetic resonance imaging (MRI) apparatus for providing magnetic resonance (MR) image, a computed tomography (CT) apparatus, an X-ray apparatus, and an ultrasound diagnostic apparatus.

In detail, MRI apparatuses photograph a subject by using a magnetic field. The MRI apparatuses are widely used to accurately diagnose a disease, because the MRI apparatuses three-dimensionally show not only bones but also discs, joints, nerves, and ligaments at a desired angle.

The MRI apparatus obtains an MR signal by using a permanent magnet, a gradient coil, and a high frequency multi-coil including radio frequency (RF) coils. Then, the MRI apparatus samples the MR signal to reconstruct an MR image.

CT apparatuses are capable of providing a cross-sectional image of an object and distinctively expressing inner structures (e.g., organs such as a kidney, a lung, etc.) of the object, compared to general X-ray apparatuses. Thus, CT apparatuses are widely used for accurately diagnosing a disease.

CT apparatuses irradiate X-rays on an object, detect X-rays that have passed through the object, and then reconstruct an image by using the detected X-rays.

As described above, medical images obtained by various medical imaging apparatuses represent an object in different ways according to the type of a medical imaging apparatus and a scanning method used.

When a medical imaging apparatus scans an object, various conditions for scanning may be referred to as 'parameters'. For example, in MRI, parameters for adjusting a contrast of an image, parameters for adjusting a resolution of an image, and parameters for adjusting an imaging sequence are available. Furthermore, these scanning conditions may be adjusted automatically or manually by a user.

In detail, during medical imaging, parameters may be edited according to a user's intention and be used to acquire a desired image. Because interdependency may exist between parameters, additional computations are used for editing parameters due to the interdependency therebetween.

Therefore, a method and apparatus for further facilitating modification of a plurality of interdependent parameters may be provided.

SUMMARY

Exemplary embodiments may address at least the above problems and/or disadvantages and other disadvantages not described above. Also, the exemplary embodiments are not required to overcome the disadvantages described above, and may not overcome any of the problems described above.

Exemplary embodiments provide methods and apparatuses for facilitating editing of a plurality of interdependent parameters.

According to an aspect of an exemplary embodiment, there is provided a method of outputting information about parameters for magnetic resonance imaging (MRI), the method comprising receiving editing information that is used to change a value of a first parameter, outputting information representing a first range of the first parameter, based on the received editing information, the first range enabling a value of a second parameter that is associated with the first parameter to be changed together with the value of the first parameter, and outputting a value to which the second parameter is changeable, according to a value to which the first parameter is changeable, based on the received editing information.

The outputting of the information representing the first range may include outputting a maximum value of the first range and a minimum value of the first range.

The method may further include outputting information representing a second range of the first parameter, based on the received editing information, the second range enabling a value of a third parameter that is associated with the second parameter to be changed together with the value of the second parameter.

The outputting of the information representing the second range may include outputting a maximum value of the second range and a minimum value of the second range.

The editing information may include the value to which the first parameter is changeable, and the method may further include outputting a value to which the third parameter is changeable, according to the value to which the first parameter is changeable.

The method may further include outputting limit value information representing a range of values to which the first parameter is not changeable.

The outputting of the limit value information may include outputting information of a fourth parameter that is associated with the first parameter and causes the limit value information.

The outputting of the information of the fourth parameter may include outputting change information of the fourth parameter that is used to change the fourth parameter and the limit value information.

The outputting of the information representing the first range may include outputting the information representing the first range in response to a cursor being positioned at an editing region of the first parameter, and the cursor may include any one or any combination of a keyboard cursor and a mouse cursor.

The outputting of the information representing the first range may include displaying a first bar comprising the first range, and the first bar may represent a range of values to which the first parameter is changeable.

The receiving of the editing information may include, in response to a cursor being positioned at the first range included in the first bar, determining the value to which the first parameter is changeable, based on a position of the cursor, and the outputting of the value to which the second parameter is changeable may include displaying the value to which the second parameter is changeable, according to the determined value to which the first parameter is changeable.

The method may further include displaying a second bar representing a range of values to which a third parameter that is associated to the first parameter is changeable. The receiving of the editing information may include receiving the value to which the first parameter is changeable. The method may further include displaying the value to which the first parameter is changeable, on the first bar, and displaying a value to which the third parameter is changeable, according to the value to which the first parameter is changeable, on the second bar.

A non-transitory computer-readable storage medium may store a program comprising instructions to cause a computer to perform the method of claim.

According to an aspect of another exemplary embodiment, there is provided an apparatus for outputting information of parameters for magnetic resonance imaging (MRI), the apparatus including an input interface configured to receive editing information that is used to change a value of a first parameter, an output interface, and a processor configured to control the output interface to output information representing a first range of the first parameter, based on the received editing information, the first range enabling a value of a second parameter that is associated with the first parameter to be changed together with the value of the first parameter, and output a value to which the second parameter is changeable, according to a value to which the first parameter is changeable, based on the received editing information.

The processor may be further configured to control the output interface to output a maximum value of the first range and a minimum value of the first range.

The processor may be further configured to control the output interface to output information representing a second range of the first parameter, based on the received editing information, the second range enabling a value of a third parameter that is associated with the second parameter to be changed together with the value of the second parameter.

The processor may be further configured to control the output interface to output a maximum value of the second range and a minimum value of the second range.

The editing information may include the value to which the first parameter is changeable, and the processor may be further configured to control the output interface to output a value to which the third parameter is changeable, according to the value to which the first parameter is changeable.

The processor may be further configured to control the output interface to output limit value information representing a range of values to which the first parameter is not changeable.

The processor may be further configured to control the output interface to output information of a fourth parameter that is associated with the first parameter and causes the limit value information.

The processor may be further configured to control the output interface to output change information of the fourth parameter that is used to change the fourth parameter and the limit value information.

The processor may be further configured to control the output interface to output the information representing the first range in response to a cursor being positioned at an editing region of the first parameter, and the cursor may include any one or any combination of a keyboard cursor and a mouse cursor.

The processor may be further configured to control the output interface to display a first bar comprising the first range, and the first bar may represent a range of values to which the first parameter is changeable.

The processor may be further configured to, in response to a cursor being positioned at the first range included in the first bar, determine the value to which the first parameter is changeable, based on a position of the cursor, and control the output interface to display the value to which the second parameter is changeable, according to the determined value to which the first parameter is changeable.

The input interface may be further configured to receive the value to which the first parameter is changeable, and the processor may be further configured to control the output interface to display a second bar representing a range of values to which a third parameter that is associated to the first parameter is changeable, display the value to which the first parameter is changeable, on the first bar, and display a value to which the third parameter is changeable, according to the value to which the first parameter is changeable, on the second bar.

According to an aspect of another exemplary embodiment, there is provided a method of outputting information of parameters for magnetic resonance imaging (MRI), the method including displaying the parameters, receiving a selection of a first parameter among the displayed parameters, displaying information representing a first range of the first parameter, based on the received selection, the first range enabling a value of a second parameter that is associated with the first parameter, among the parameters, to be changed together with a value of the first parameter, receiving a value to which the first parameter is changeable, and displaying a value to which the second parameter is changeable, based on the received value to which the first parameter is changeable.

The receiving of the value to which the first parameter is changeable may include receiving a position of a cursor that is positioned at the first range, and determining the value to which the first parameter is changeable, based on the received position.

BRIEF DESCRIPTION OF THE DRAWINGS

The above and/or other aspects will be more apparent by describing exemplary embodiments with reference to the accompanying drawings, in which:

FIG. 6 is a diagram illustrating an editing window for parameters for magnetic resonance (MR) image scanning, according to an exemplary embodiment;

DETAILED DESCRIPTION

Figure 1:
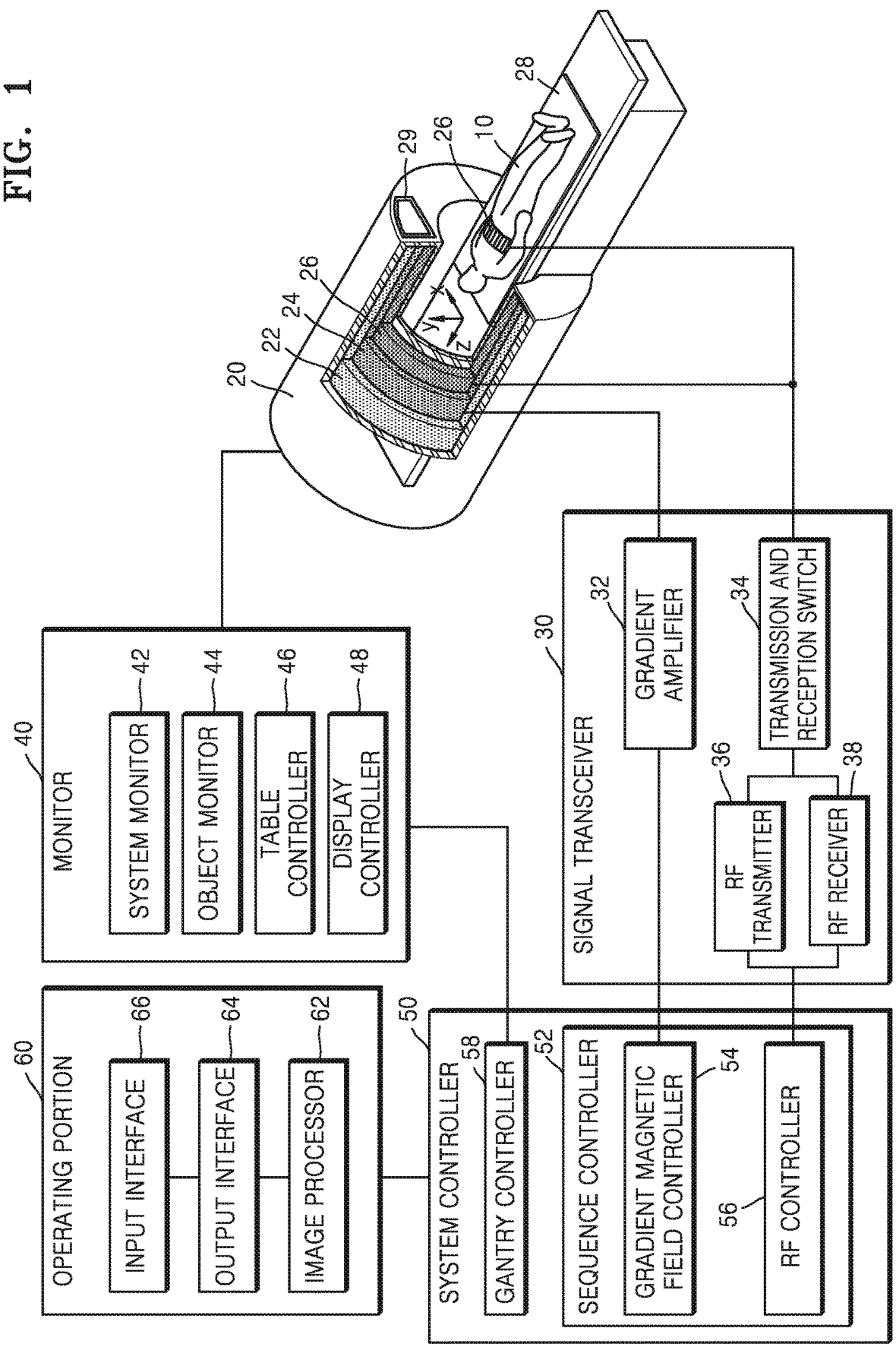
FIG. 1 is a schematic diagram of a general magnetic resonance imaging (MRI) system.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail because they would obscure the description with unnecessary detail.

When a part "includes" or "comprises" an element, unless there is a description contrary thereto, the part can further include other elements, not excluding the other elements. Also, the term "unit" in the exemplary embodiments means a software component or hardware component such as a field-programmable gate array (FPGA) or an application-specific integrated circuit (ASIC), and performs a specific function. However, the term "unit" is not limited to software or hardware. The "unit" may be formed to be in an addressable storage medium, or may be formed to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units," or may be divided into additional components and "units."

Throughout the specification, an "image" may denote multi-dimensional data composed of discrete image elements (for example, pixels in a two-dimensional image and voxels in a three-dimensional image). For example, the image may be a medical image of an object scanned by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

Further, in the present specification, the term "conflict" between parameters refers to a case in which, when the value of a parameter is changed, another parameter that is to be changed together based on the MR physics for scanning for an MR image exists. For example, when the value of a Field of View (FoV) Read value is changed, a time to echo (TE) may be changed together. When the TE is changed, a repetition time (TR) may be changed together.

An MRI system is an apparatus for acquiring a sectional image of a part of an object by expressing, in a contrast comparison, a strength of a MR signal with respect to a radio frequency (RF) signal generated in a magnetic field having a strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are used to precisely scan abnormal tissues.

FIG. 1 is a schematic diagram of a general MRI system. Referring to FIG. 1, the general MRI system may include a gantry 20, a signal transceiver 30, a monitor 40, a system controller 50, and an operating portion 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 may further include a display 29 disposed outside the gantry 20 and a display disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitor 40 may monitor or control the gantry 20 or devices mounted on the gantry 20. The monitor 40 may include a system monitor 42, an object monitor 44, a table controller 46, and a display controller 48.

The system monitor 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitor 44 monitors a state of the object 10. In detail, the object monitor 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 on which the object 10 is positioned. The table controller 46 may control the movement of the table 28 according to a sequence control of a sequence controller 50. For example, during moving imaging of the object 10, the table controller 46 may continuously or discontinuously move the table 28 according to the sequence control of the sequence controller 50, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system controller 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating portion 60. Here, the pulse sequence includes all information used to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating portion 60 may request the system controller 50 to transmit pulse sequence information while controlling an overall operation of the MRI system.

The operating portion 60 may include an image processor 62 for receiving and processing the MR signal received by the RF receiver 38, an output interface 64, and an input interface 66.

The image processor 62 may process the MR signal received from the RF receiver 38 to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space (for example, also referred to as a Fourier space or a frequency space) of a memory, and rearrange the digital data into image data via 2D or 3D Fourier transformation.

The image processor 62 may perform a composition process or difference calculation process on the image data. The composition process may be an addition process performed on a pixel or a maximum intensity projection (MIP) process performed on a pixel. The image processor 62 may store not only the rearranged image data but also image data on which a composition process or a difference calculation process is performed, in a memory or an external server.

The image processor 62 may perform any of the signal processes on the MR signal in parallel. For example, the image processor 62 may perform a signal process on a plurality of MR signals received by a multi-channel RF coil in parallel to rearrange the plurality of MR signals into image data.

The output interface 64 may output image data generated or rearranged by the image processor 62 to the user. The output interface 64 may also output information used for the user to manipulate the MRI system, such as a user interface (UI), user information, or object information. The output interface 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, a transparent display, or any one of other various output devices that are well known to one of ordinary skill in the art.

The user may input object information, parameter information, a scan condition, a pulse sequence, or information about image composition or difference calculation by using the input interface 66. The input interface 66 may be a keyboard, a mouse, a track ball, a voice recognizer, a gesture recognizer, a touch screen, or any one of other various input devices that are well known to one of ordinary skill in the art.

The signal transceiver 30, the monitor 40, the system controller 50, and the operating portion 60 are separate components in FIG. 1, but it will be obvious to one of ordinary skill in the art that respective functions of the signal transceiver 30, the monitor 40, the system controller 50, and the operating portion 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitor 40, the system controller 50, and the operating portion 60 may be connected to each other by wire or wirelessly, and when they are connected wirelessly, the MRI system may further include an apparatus for synchronizing clock signals therebetween. Communication between the gantry 20, the RF coil 26, the signal transceiver 30, the monitor 40, the system controller 50, and the operating portion 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any of other various communication methods that are well known to one of ordinary skill in the art.

Figure 2:
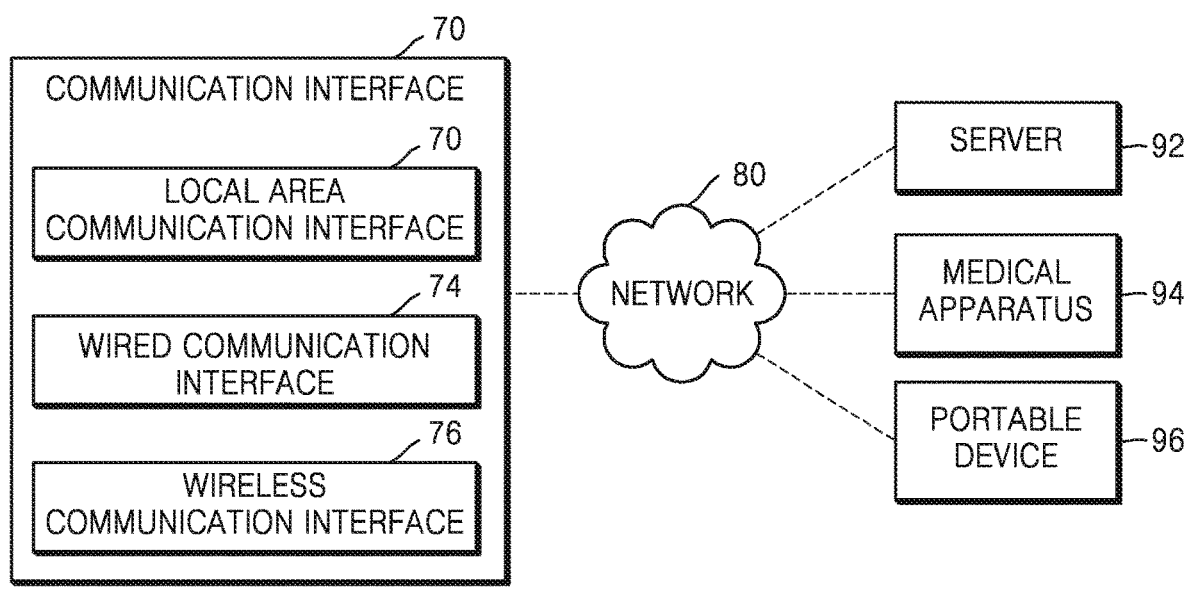
FIG. 2 is a schematic diagram illustrating a structure of a communication interface according to an exemplary embodiment.

FIG. 2 is a schematic diagram illustrating a structure of a communication interface 70 according to an exemplary embodiment. Referring to FIG. 2, the communication interface 70 may be connected to at least one selected from the gantry 20, the signal transceiver 30, the monitor 40, the system controller 50, and the operating portion 60 of FIG. 1.

The communication interface 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 2, the communication interface 70 may be connected to a network 80 by wire or wirelessly to communicate with a server 92, a medical apparatus 94, or a portable device 96.

In detail, the communication interface 70 may transmit and receive data related to the diagnosis of an object through the network 80, and may also transmit and receive a medical image captured via scanning by the medical apparatus 94, such as a CT apparatus, an MRI apparatus, or an X-ray apparatus. In addition, the communication interface 70 may receive a diagnosis history or a treatment schedule of the object from the server 92 and use the same to diagnose the object. The communication interface 70 may perform data communication not only with the server 92 or the medical apparatus 94 in a hospital, but also with the portable device 96, such as a mobile phone, a personal digital assistant (PDA), or a laptop of a doctor or patient.

Also, the communication interface 70 may transmit information about a malfunction of the MRI system or about a medical image quality to a user through the network 80, and receive a feedback regarding the information from the user.

The communication interface 70 may include at least one component enabling communication with an external apparatus.

For example, the communication interface 70 may include a local area communication interface 72, a wired communication interface 74, and a wireless communication interface 76. Examples of local area communication techniques according to an exemplary embodiment may include, but are not limited to, wireless LAN, Wi-Fi, Bluetooth, zigbee, Wi-Fi Direct (WFD), ultra wideband (UWB), infrared data association (IrDA), Bluetooth low energy (BLE), and near field communication (NFC).

The wired communication interface 74 refers to an interface for performing communication by using an electric signal or an optical signal. Examples of wired communication technology according to an exemplary embodiment include wired communication techniques using a pair cable, a coaxial cable, and an optical fiber cable, and other well known wired communication techniques.

The wireless communication interface 76 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

In the MRI system described with reference to FIGS. 1 and 2, various parameters may be adjusted during scanning to obtain an MR image by scanning an object. Examples of parameters that are to be adjusted may include the number of slices, a slice gap, a position that is to be scanned, orientation, a phase encoding direction, phase oversampling, and a slice thickness. Various other examples of the parameters may exist according to types, specifications and/or functions of the MRI system.

As described above, when one of a plurality of parameters having interdependency therebetween is changed to a value, values of other parameters that are dependent upon the changed parameter may be newly calculated and changed. Furthermore, if the values of other parameters that are dependent on the changed parameter are automatically changed, a user interface (UI) is output that allows a user to more easily identify the changed parameter and a change history.

A method and apparatus for providing an editing history notifying a change or modification of a plurality of parameters that are dependent upon one another and editing parameters by using the editing history will now be described in detail.

Figure 3:
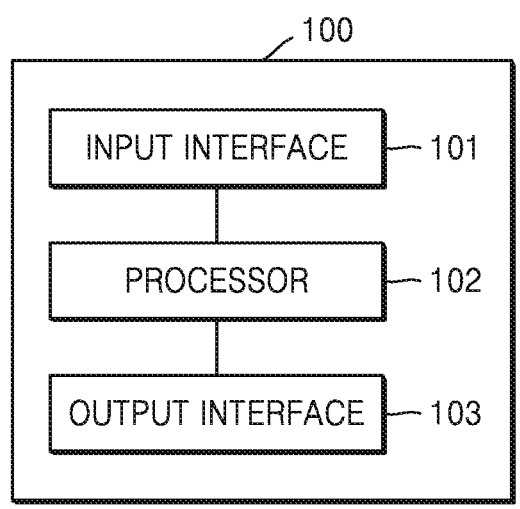
FIG. 3 is a block diagram of a parameter information outputting apparatus according to an exemplary embodiment.

FIG. 3 is a block diagram of a parameter information outputting apparatus 100 according to an exemplary embodiment. The parameter information outputting apparatus 100 may be any electronic apparatus capable of performing at least one operation among scanning and acquiring of a medical image by adjusting parameters. In detail, the medical image may include any image that may be used in diagnosis of an object, such as an MR image, a tomography image, or an ultrasound image. In detail, the parameter information outputting apparatus 100 of FIG. 3 may be included in the MRI system described with reference to FIGS. 1 and 2. Furthermore, the parameter information outputting apparatus 100 of FIG. 3 may correspond to any one or any combination of the server 92, the medical apparatus 94, and the portable device 96 described with reference to FIG. 2.

Referring to FIG. 3, the parameter information outputting apparatus 100 may include an input interface 101, a processor 102, and an output interface 103.

When the parameter information outputting apparatus 100 is included in the MRI system described with reference to FIGS. 1 and 2, the processor 102 may correspond to a part or the entire portion of any one or any combination of the system controller 50 and the monitor 40. The input interface 101 may correspond to the input interface 66 of FIG. 1. The output interface 103 may correspond to the output interface 64 of FIG. 1.

The input interface 101 may include a keyboard, a mouse, a track ball, a voice recognizer, a gesture recognizer, or a touch screen, or may include any one of other various input interfaces that are well known to one of ordinary skill in the art.

The input interface 101 receives editing information used to change a first parameter for medical image scanning. The editing information used to change a first parameter may include a selection input of selecting the first parameter, and a change value for changing the first parameter.

According to an exemplary embodiment, the output interface 103 may include any one or any combination of a speaker, a printer, and a display.

In detail, examples of the display included in the output interface 103 may include a cathode ray tube (CRT) display, a liquid crystal display (LCD), a plasma display panel (PDP) display, an organic light-emitting diode (OLED) display, a field emission display (FED), a light-emitting diode (LED) display, a vacuum fluorescent display (VFD), a digital light processing (DLP) display, a flat panel display (FPD), a three-dimensional (3D) display, a transparent display, and various other output interfaces that are obvious to one of ordinary skill in the art.

The output interface 103 outputs information representing a first range, based on the editing information received by the input interface 101, when the value of a second parameter associated with the first parameter is changed as the first parameter is changed to a value within the first range.

The output interface 103 also outputs a value to which the second parameter is to be changed according to the value to which the first parameter is changed, based on the editing information received by the input interface 101.

According to an exemplary embodiment, the display included in the output interface 103 may display information representing the first range, for example, a screen image including the information representing the first range.

The processor 102 controls the input interface 101 and the output interface 103. The processor 102 may acquire the editing information used to change the first parameter from the input interface 101. The processor 102 may control the information representing the first range to be output when the value of a second parameter associated with the first parameter is changed as the first parameter is changed to a value within the first range, based on the editing information.

The processor 102 may also control outputting of the value to which the second parameter is to be changed according to the value to which the first parameter is changed, based on the editing information.

An operation of the parameter information outputting apparatus 100 according to an exemplary embodiment will now be described in detail with reference to FIGS. 4-12.

Figure 4:
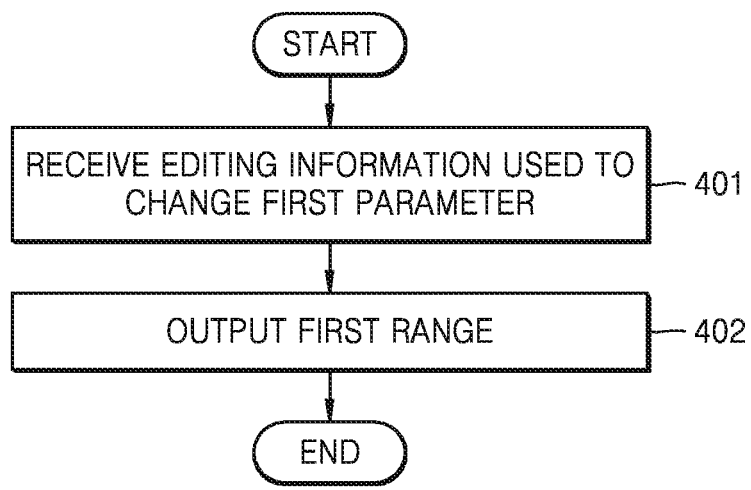
FIG. 4 is a flowchart of a parameter editing method according to an exemplary embodiment.

FIG. 4 is a flowchart of a parameter editing method according to an exemplary embodiment.

The parameter editing method according to an exemplary embodiment may be performed by the parameter information outputting apparatus 100 of FIG. 3, and may be the same as an operation of the parameter information outputting apparatus 100.

In operation 401, the parameter information outputting apparatus 100 receives editing information used to change a first parameter. The editing information used to change a first parameter may include a selection input of selecting the first parameter, and a change value for changing the first parameter. Operation 401 may be performed by the input interface 101 of the parameter information outputting apparatus 100.

In operation 402, the parameter information outputting apparatus 100 outputs a first range, based on the editing information received in operation 401. The first range refers to a predetermined value range of the first parameter when the value of a second parameter associated with the first parameter is changed together with the first parameter.

The parameter information outputting apparatus 100 outputs a value to which the second parameter is to be changed according to the value to which the first parameter is changed, based on the editing information received in operation 401. Operation 402 may be performed by the output interface 103 of the parameter information outputting apparatus 100.

Operations 401 and 402 may be controlled by the processor 102 of the parameter information outputting apparatus 100.

Figure 5:
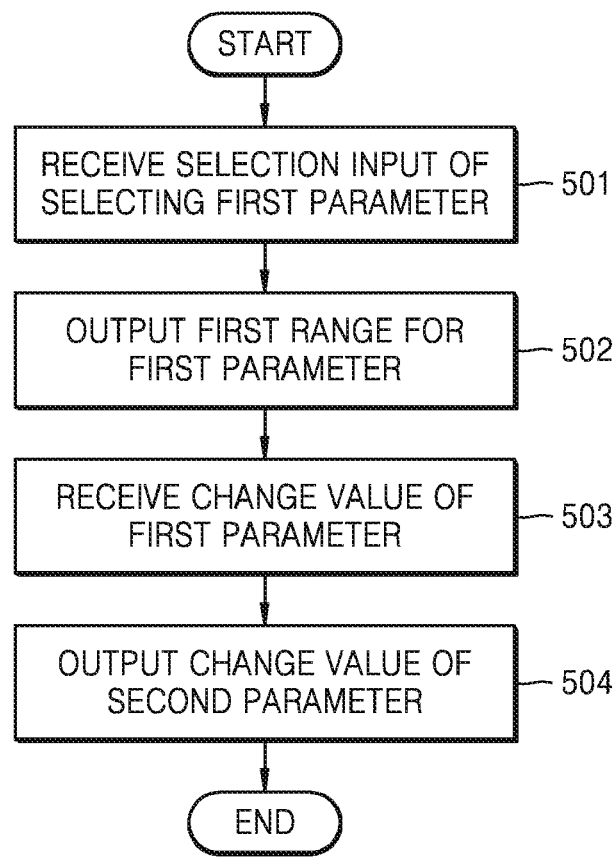
FIG. 5 is a flowchart of a parameter editing method according to an exemplary embodiment.

FIG. 5 is a flowchart of a parameter editing method according to an exemplary embodiment.

The parameter editing method according to an exemplary embodiment may be performed by the parameter information outputting apparatus 100 of FIG. 3, and may be the same as an operation of the parameter information outputting apparatus 100.

In operation 501, the parameter information outputting apparatus 100 receives a selection input of selecting a first parameter. For example, the parameter information outputting apparatus 100 may receive a selection input of clicking an editing region for the first parameter with a mouse.

According to another exemplary embodiment, the parameter information outputting apparatus 100 may determine whether a cursor is positioned at the editing region for the first parameter. If the cursor is positioned at the editing region for the first parameter, the parameter information outputting apparatus 100 may determine that the first parameter has been selected. The cursor may include any one or any combination of a keyboard cursor and a mouse cursor.

The parameter information outputting apparatus 100 may control a preview menu for a first range corresponding to a parameter focused using the input interface 101 to be displayed. In other words, the parameter information outputting apparatus 100 may provide a preview menu so that a user may receive reference information used to select a predetermined parameter even before the first parameter is selected. When the preview menu is provided, the user may check a first range corresponding to the predetermined parameter via the preview menu and may finally select the first parameter in consideration of the first range.

In operation 502, the parameter information outputting apparatus 100 outputs a first range for the first parameter. The first range refers to a predetermined value range of the first parameter that enables the value of a second parameter associated with the first parameter to be changed when the first parameter is changed to a value within the predetermined range. According to an exemplary embodiment, the parameter information outputting apparatus 100 may display a screen image including information representing the first range.

According to an exemplary embodiment, the parameter information outputting apparatus 100 may output information including a first threshold value representing a maximum value of the first range and a second threshold value representing a minimum value of the first range. The parameter information outputting apparatus 100 may display a screen image including the first threshold value and the second threshold value.

In operation 503, the parameter information outputting apparatus 100 receives a change value of the first parameter. For example, the parameter information outputting apparatus 100 may receive a change value of the first parameter via a keyboard. As another example, the parameter information outputting apparatus 100 may receive a change value of the first parameter via a mouse.

In operation 504, the parameter information outputting apparatus 100 outputs a change value of the second parameter, based on the change value of the first parameter received in operation 503. For example, the parameter information outputting apparatus 100 may output the change value of the second parameter when the value of the first parameter is changed to a value within the first range. The parameter information outputting apparatus 100 may display a screen image including the change value of the second parameter.

FIG. 6 is a diagram illustrating an editing window for parameters for MR image scanning, according to an exemplary embodiment. According to an exemplary embodiment, a parameter editing window 600 may include parameters, such as a FoV Read 610, a FoV Phase 620, a TR 630, and a TE 640.

FoV denotes a region that is to be scanned. The FoV Read 610 and the FoV Phase 620 are parameters for determining an FoV. The FoV Read 610 represents the size of a region that is shown, and the FoV Phase 620 denotes a viewing angle. According to an exemplary embodiment, the FoV Read 610 and the FoV Phase 620 are parameters associated with each other. Thus, when a FoV is adjusted, the values of the FoV Read 610 and the FoV Phase 620 may be changed together.

The TR 630 and the TE 640 denote a repetition time (TR) or a time to echo (TE), respectively. The TR 630 and the TE 640 are parameters associated with each other, and thus the values of the TR 630 and the TE 640 may be changed together according to change ranges. The FoV Read 610 and the TE 640 are parameters associated with each other, and the values of the FoV Read 610 and the TE 640 may be changed together according to change ranges.

Figure 7:
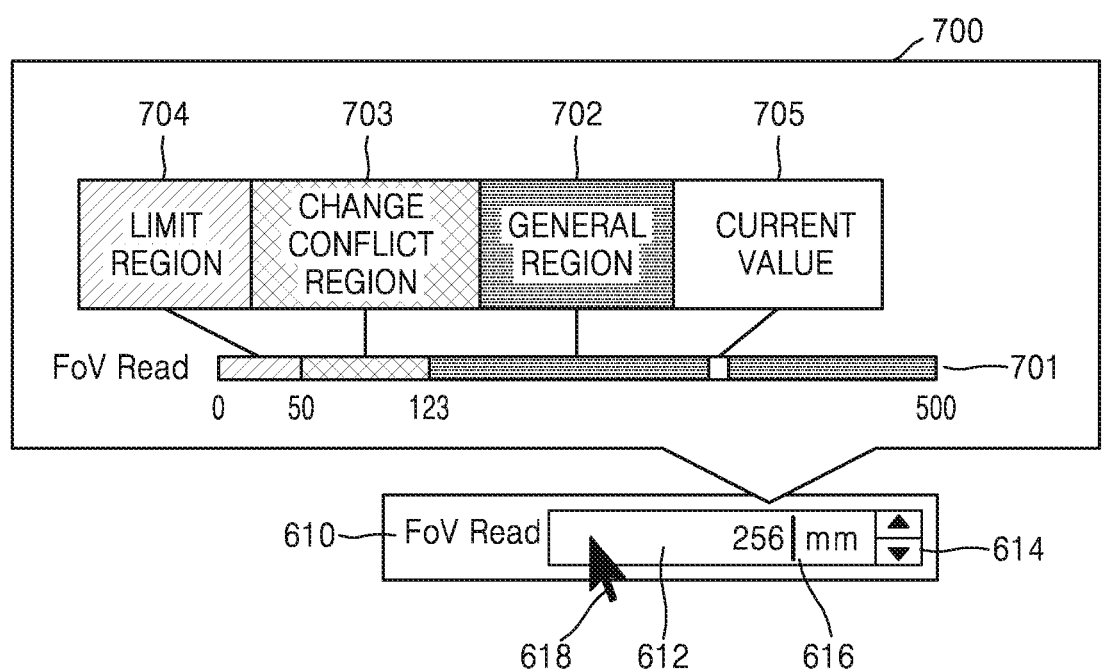
FIG. 7 is a diagram illustrating a screen image including a first range, according to an exemplary embodiment.

FIG. 7 is a diagram illustrating a screen image including a first range, according to an exemplary embodiment. According to an exemplary embodiment, the screen image including the first range may be displayed in the form of a window. A window 700 may include a first bar 701 representing the range of values that the first parameter may have. For example, the first parameter may be the FoV read 610.

According to an exemplary embodiment, the first bar 701 may include a general region 702, a change conflict region 703, and a limit region 704. The first bar 701 may also include a current value 705 of the first parameter. The first bar 701 may include threshold values corresponding to both end values of each region.

The general region 702 may represent a value range in which other parameters are not changed even when the first parameter is changed. In other words, the general region 702 corresponds to the value range of the first parameter that prevents a change in a parameter associated with the first parameter even when the first parameter is changed. For example, when the value of the FoV read 610 is changed between 123 and 500, the values of other parameters may not be changed.

The change conflict region 703 may correspond to the first range disclosed in the present specification. In other words, the change conflict region 703 corresponds to the value range of the first parameter that enables a parameter associated with the first parameter to be changed when the first parameter is changed. For example, when the value of the FoV read 610 is changed to no more than 123 and no less than 50, the values of other parameters may be changed.

The limit region 704 may correspond to a region that deviates from a limit value disclosed in the present specification. In the present specification, the limit value may represent any one or any combination of a maximum value and a minimum value to which the first parameter may be changed. For example, the value of the FoV Read 610 may not be able to be changed to less than 50. In detail, when an FoV is to be at least a predetermined minimum region during MR image scanning according to a predetermined protocol, the FoV is set to be at least the predetermined minimum region, and the value of the FoV read 610 is also set to be at least a predetermined value. Accordingly, because the parameter information outputting apparatus 100 is to change the value of the FoV Read 610 within only a range that enables the value of the FoV Read 610 to be at least the predetermined value, parameter information outputting apparatus 100 may set the predetermined value to be a minimum limit value.

According to another exemplary embodiment, the window 700 may be displayed in such a form as Table 1 below. A method of displaying the general region 702, the change conflict region 703, the limit region 704, and threshold values of each region is not limited, and all possible methods may be used.

TABLE 1

| | |
|---|---|
| Current value | 256 |
| Change conflict threshold value | 123 |
| Limit value | 50 |
| Maximum value | 500 |

According to an exemplary embodiment, the window 700 may be displayed in response to a selection input to the first parameter. For example, the parameter information outputting apparatus 100 may display the window 700 in response to selection inputs to parameter editing regions 612 and 614 of the FoV Read 610.

For example, the parameter information outputting apparatus 100 may display the window 700 when a mouse cursor 618 is positioned on the parameter editing regions 612 and 614 of the FoV Read 610. As another example, the parameter information outputting apparatus 100 may display the window 700 when click inputs to the parameter editing regions 612 and 614 of the FoV Read 610 are received.

As another example, the parameter information outputting apparatus 100 may display the window 700 when a keyboard cursor 616 is positioned on the parameter editing region 612 of the FoV Read 610. The location at which and form in which the window 700 is displayed are not limited, and the window 700 may be displayed in all possible forms.

Figure 8:
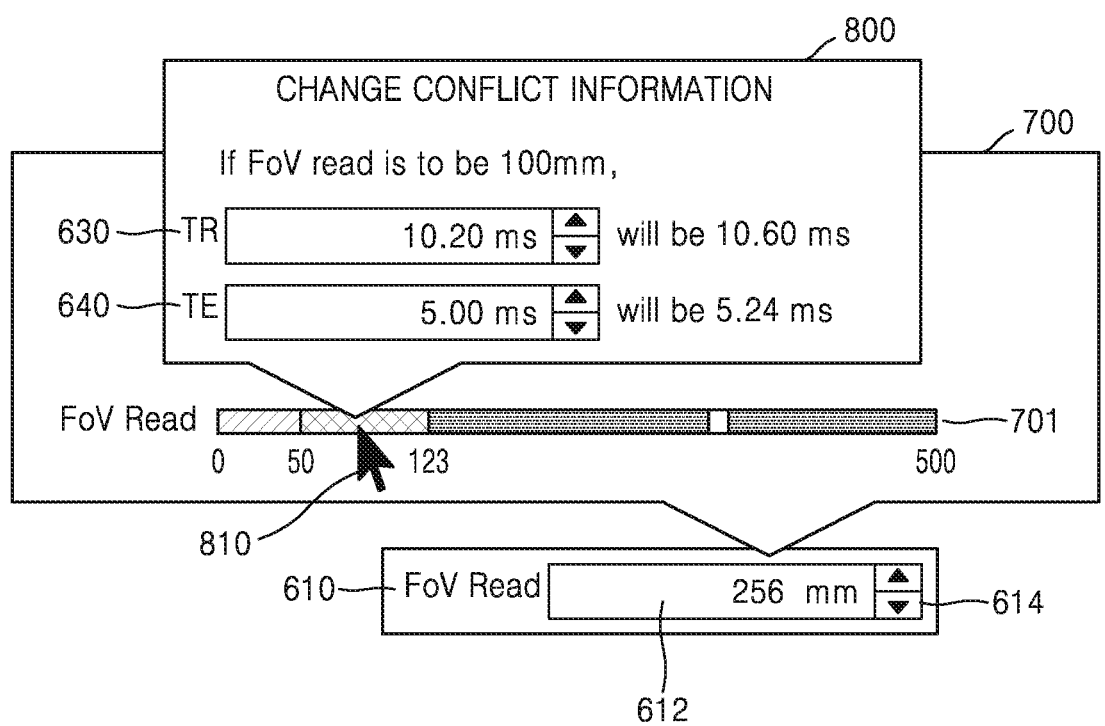
FIG. 8 is a diagram illustrating a screen image including a change value of a second parameter, according to an exemplary embodiment.

FIG. 8 is a diagram illustrating a screen image including a change value of a second parameter, according to an exemplary embodiment. According to an exemplary embodiment, the screen image including the change value of the second parameter may be displayed in the form of a window. A window 800 may include a current value and a change value of a second parameter. The second parameter denotes a parameter associated with the first parameter.

When a plurality of parameters are also changed when the first parameter is changed, namely, when a plurality of second parameters are associated with the first parameter, the window 800 may include a plurality of parameters. For example, the window 800 may include the parameters that are also changed when the FoV Read 610 is changed, namely, the TR 630 and the TE 640.

The parameter information outputting apparatus 100 may receive a change value for changing the first parameter. For example, when a mouse cursor 810 is positioned on the change conflict region 703 included in the first bar 701, the parameter information outputting apparatus 100 may determine a value corresponding to the location of the mouse cursor 810 as the change value of the first parameter.

According to another exemplary embodiment, the parameter information outputting apparatus 100 may receive a change value of the first parameter input to the parameter editing region 612. As another example, the parameter information outputting apparatus 100 may receive an input of clicking a button included in the parameter editing region 614 and thus may determine the change value of the first parameter.

According to an exemplary embodiment, the parameter information outputting apparatus 100 may display the window 800 in response to receiving the change value for changing the first parameter. However, the location at which and form in which the window 800 is displayed are not limited, and the window 800 may be displayed in all possible forms.

The window 800 may include a value to which the second parameter is to be changed and that is calculated based on the change value of the first parameter. For example, when the change value of the FoV Read 610 is 100 mm, the TE 640 may be changed from 5.00 ms to 5.24 ms, and the TR 630 may be changed from 10.20 ms to 10.60 ms.

According to an exemplary embodiment, the parameter information outputting apparatus 100 may calculate and display values to which the values of the TR 630 and the TE 640 are to be changed according to a value to which the value of the FoV Read 610 is changed, before the values of associated parameters are actually changed according to a change in the first parameter.

According to an exemplary embodiment, the parameter information outputting apparatus 100 may display an example of a scan result image according to the value to which a parameter is to be changed. For example, the parameter information outputting apparatus 100 may include a database including an example of a scan result image according to each parameter value.

According to an exemplary embodiment, the parameter information outputting apparatus 100 may receive a change value for changing the first parameter. The parameter information outputting apparatus 100 may acquire a value to which at least one parameter including the second parameter is to be changed, based on the change value of the first parameter.

The parameter information outputting apparatus 100 may acquire an example of a scan result image corresponding to the change value of the first parameter and the value to which at least one parameter is to be changed, from the database.

The parameter information outputting apparatus 100 may display the example of the scan result image acquired from the database. According to an exemplary embodiment, a user may easily predict an effect due to a parameter change.

Figure 9:
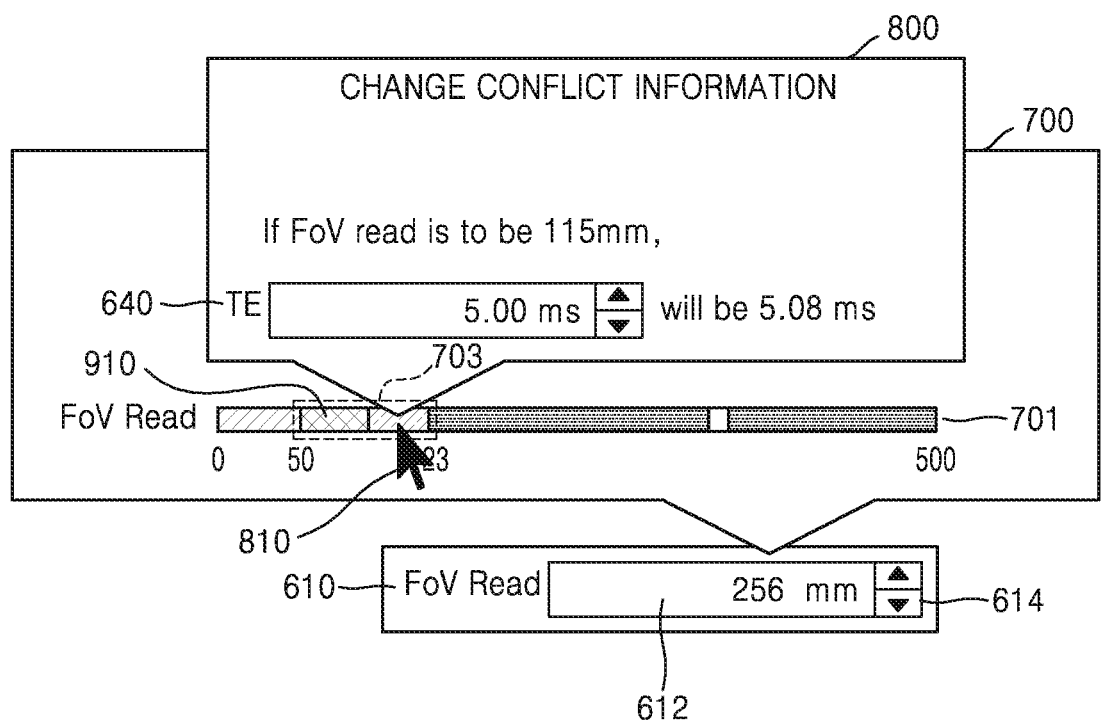
FIG. 9 is a diagram illustrating a method of displaying a screen image including a second range, according to an exemplary embodiment.

FIG. 9 is a diagram illustrating a method of displaying a screen image including a second range, according to an exemplary embodiment. The second range refers to a predetermined value range of the first parameter that enables the value of a third parameter associated with the second parameter to be changed together with the second parameter when the first parameter is edited to a value within the predetermined range. Accordingly, according to an exemplary embodiment, the second range may be included in the first range.

For example, the TR 630 is not a parameter directly associated with the FoV Read 610. However, the TE 640 is associated with the FoV Read 610, and the TR 630 is associated with the TE 640. Accordingly, when the TE 640 is changed by the FoV Read 610 by a predetermined value or greater, the TR 630 may be changed together with the TE 640.

In the present example, the TR 630 may correspond to the third parameter, and the TE 640 may correspond to the second parameter. In this case, the parameter information outputting apparatus 100 may determine a value range of the FoV Read 610 that enables the TR 630 to be also changed, to be the second range.

Referring to FIG. 9, the first bar 701 may include a second change conflict region 910. The second change conflict region 910 may correspond to the second range disclosed in the present specification.

According to an exemplary embodiment, the parameter information outputting apparatus 100 may output information including a first threshold value representing a maximum value of the first range and a second threshold value representing a minimum value of the first range. The parameter information outputting apparatus 100 may display a screen image including the first threshold value and the second threshold value.

The parameter information outputting apparatus 100 may also output information including a third threshold value representing a maximum value of the second range and a fourth threshold value representing a minimum value of the second range. The parameter information outputting apparatus 100 may display a screen image including the third threshold value and the fourth threshold value.

According to an exemplary embodiment, the parameter information outputting apparatus 100 may receive a change value for changing the first parameter.

Referring to FIG. 9, when the mouse cursor 810 is positioned on the first bar 701, the parameter information outputting apparatus 100 may determine a value corresponding to the location of the mouse cursor 810 as the change value of the first parameter.

According to another exemplary embodiment, the parameter information outputting apparatus 100 may receive a change value of the first parameter input to the parameter editing region 612. As another example, the parameter information outputting apparatus 100 may receive an input of clicking a button included in the parameter editing region 614 and thus may determine the change value of the first parameter.

When the change value of the first parameter is included in the first range and not included in the second range, the parameter information outputting apparatus 100 may output a change value of the second parameter. For example, the parameter information outputting apparatus 100 may display a screen image including the change value of the second parameter. For example, when the change value of the FoV Read 610 is 115 mm, the TE 640 may be changed from 5.00 ms to 5.08 ms.

According to an exemplary embodiment, the parameter information outputting apparatus 100 may calculate and display a value to which the value of the TE 640 is to be changed according to a value to which the value of the FoV Read 610 is changed, without actually changing the values of associated parameters.

According to another exemplary embodiment, the window 800 may be displayed in such a form as Table 2 below. A method of displaying the general region 702, the change conflict region 703, the second change conflict region 910, the limit region 704, and threshold values of each region is not limited, and all possible methods may be used.

TABLE 2

| | |
|---|---|
| Current value | 256 |
| Change conflict threshold value | 123 |
| Second change conflict threshold value | 110 |
| Limit value | 50 |
| Maximum value | 500 |

Figure 10:
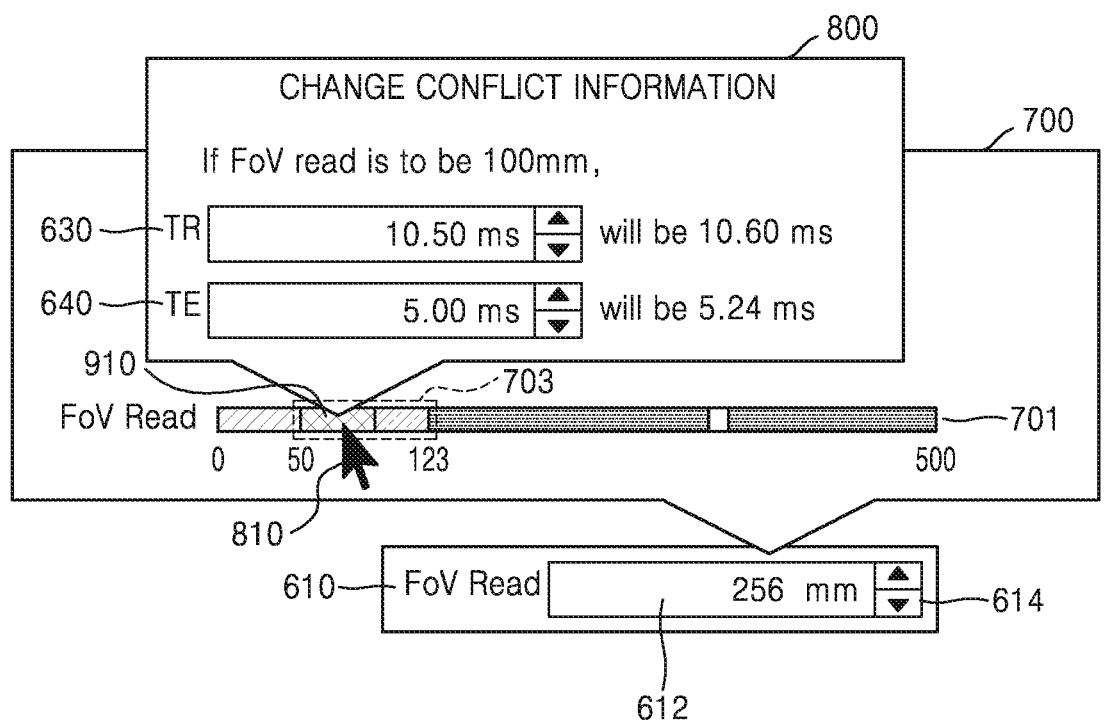
FIG. 10 is a diagram illustrating a case in which a change value of a first parameter is included in a second range, according to an exemplary embodiment.

FIG. 10 is a diagram illustrating a case in which a change value of a first parameter is included in a second range, according to an exemplary embodiment. According to an exemplary embodiment, the parameter information outputting apparatus 100 may receive a change value for changing the first parameter.

Referring to FIG. 10, when the mouse cursor 810 is positioned on the first bar 701, the parameter information outputting apparatus 100 may determine a value corresponding to the location of the mouse cursor 810 as the change value of the first parameter.

According to another exemplary embodiment, the parameter information outputting apparatus 100 may receive a change value of the first parameter input to the parameter editing region 612. As another example, the parameter information outputting apparatus 100 may receive an input of clicking a button included in the parameter editing region 614 and thus may determine the change value of the first parameter.

When the change value of the first parameter is included in the second range, the parameter information outputting apparatus 100 may output change values of the second and third parameters. For example, the parameter information outputting apparatus 100 may display a screen image including the change value of the second parameter.

For example, when the change value of the FoV Read 610 is 115 mm, the TE 640 may be changed from 5.00 ms to 5.08 ms. For example, when the change value of the FoV Read 610 is 100 mm, the TE 640 may be changed from 5.00 ms to 5.24 ms. The TR 630 may be changed from 10.20 ms to 10.60 ms due to the change value of the TE 640.

According to an exemplary embodiment, the parameter information outputting apparatus 100 may calculate and display a value to which the value of the TE 640 is to be changed according to a value to which the value of the FoV Read 610 is changed, without actually changing the values of associated parameters. The parameter information outputting apparatus 100 may also calculate and display a value to which the value of the TR 630 is to be changed according to a value to which the value of the TE 640 is changed.

Figure 11:
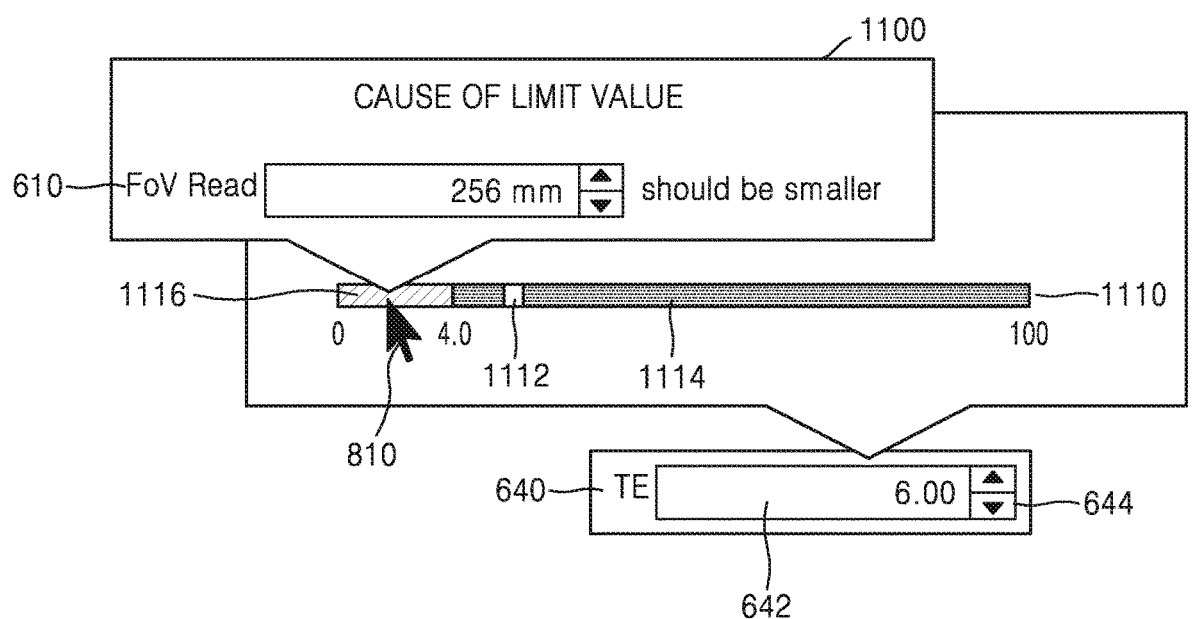
FIG. 11 is a diagram illustrating a screen image including limit value information, according to an exemplary embodiment.

FIG. 11 is a diagram illustrating a screen image including limit value information, according to an exemplary embodiment. According to an exemplary embodiment, the first parameter may not be able to be changed to be no more than or no less than a predetermined limit value.

Referring to FIG. 11, the TE 640 may correspond to the first parameter. According to an exemplary embodiment, when the FoV Read 610 is set to be 256 mm, the TE 640 may not be able to be 4.5 ms or less.

In the present example, the FoV Read 610, which is a parameter that causes the TE 640 to be not changed to 4.5 ms or less, may correspond to a fourth parameter disclosed in the present specification. The parameter information outputting apparatus 100 may output information about the fourth parameter. The parameter information outputting apparatus 100 may also output change information of the fourth parameter used to change a limit value of the first parameter.

According to an exemplary embodiment, the parameter information outputting apparatus 100 may display a screen image including the fourth parameter. The parameter information outputting apparatus 100 may also output change information of the fourth parameter used to change a limit value of the first parameter.

For example, in order for the TE 640 to be changed to 4.5 or less, the FoV Read 610 may be smaller than a current value. In this case, the parameter information outputting apparatus 100 may output information indicating that the FoV Read 610 is to be smaller than a current value.

Referring to FIG. 11, the parameter information outputting apparatus 100 may display a first bar 1110 representing the range of values that the first parameter may have. The first bar 1110 may include a current value 1112, a general region 1114, and a limit region 1116. The limit region 1116 may correspond to a range that uses the limit value disclosed in the present specification as a threshold value.

The parameter information outputting apparatus 100 may receive a change value for changing the first parameter. For example, when the mouse cursor 810 is positioned on the first bar 1110, the parameter information outputting apparatus 100 may determine a value corresponding to the location of the mouse cursor 810 as the change value of the first parameter.

According to another exemplary embodiment, the parameter information outputting apparatus 100 may receive a change value of the first parameter input to a parameter editing region 642. As another example, the parameter information outputting apparatus 100 may receive an input of clicking a button included in a parameter editing region 644 and thus may determine the change value of the first parameter.

When the change value of the first parameter deviates from the limit value, the parameter information outputting apparatus 100 may display a window 1100 including a cause of the limit value. The window 1100 may include information about the fourth parameter serving as the cause of the limit value of the first parameter and the change information of the fourth parameter used to change the limit value of the first parameter.

A form and a method in which values that the first parameter may have are displayed are not limited, and all possible forms and methods may be used. A form and a method in which the window 1100 is displayed are not limited, and all possible forms and methods may be used.

Figure 12:
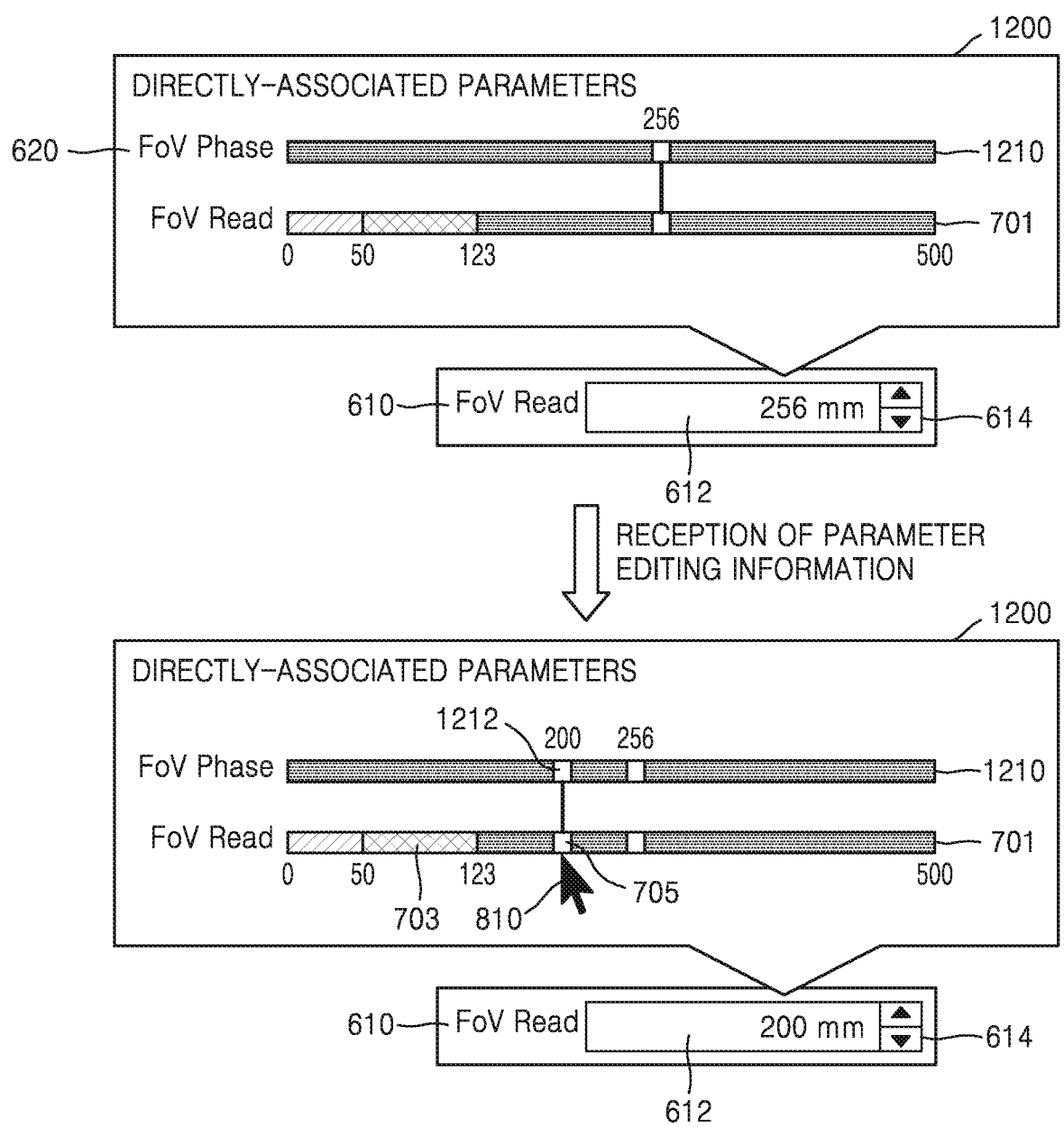
FIG. 12 is a diagram illustrating a screen image including directly associated parameters, according to an exemplary embodiment.

FIG. 12 is a diagram illustrating a screen image including directly associated parameters, according to an exemplary embodiment. In the present specification, the directly associated parameters denote parameters of which values are to be changed together all the time regardless of value ranges because they are closely associated with each other. For example, the FoV Read 610 and the FoV Phase 620 are directly associated parameters.

Referring to FIG. 12, the parameter information outputting apparatus 100 may display a window 1200 including directly associated parameters. The window 1200 may include the first bar 701 representing the range of values that the first parameter may have, and a second bar 1210 representing the range of values that the third parameter directly associated with the first parameter may have.

According to an exemplary embodiment, the parameter information outputting apparatus 100 may receive a change value for changing the first parameter.

Referring to FIG. 12, when the mouse cursor 810 is positioned on the first bar 701, the parameter information outputting apparatus 100 may determine a value corresponding to the location of the mouse cursor 810 as the change value of the first parameter. For example, when mouse click information for the first bar 701 is received, the parameter information outputting apparatus 100 may determine a value corresponding to the location of the mouse click as the change value of the first parameter.

According to another exemplary embodiment, the parameter information outputting apparatus 100 may receive a change value of the first parameter input to a parameter editing region 612. As another example, the parameter information outputting apparatus 100 may receive an input of clicking a button included in the parameter editing region 614 and thus may determine the change value of the first parameter.

The parameter information outputting apparatus 100 may display a change value of the third parameter corresponding to the change value of the first parameter on the second bar 1210. For example, the window 1200 before parameter editing information is received may include the first bar 701 and the second bar 1210.

The first bar 701 and the second bar 1210 may include the current value 705 of the first parameter and a current value 1212 of the third parameter, respectively. For example, the first parameter may be the FoV Read 610, and the third parameter may be the FoV Phase 620.

The FoV Read 610 and the FoV Phase 620 may both have a value of 256 mm before the parameter editing information is received. If a change value of the FoV Read 610 according to the received parameter editing information is 200 mm, the value of the FoV Phase 620 may also be changed to 200 mm.

The first bar 701 and the second bar 1210 may include the current value 705 of the changed first parameter and a value 1212 of the changed third parameter, respectively. According to an exemplary embodiment, the parameter information outputting apparatus 100 may display the value 1212 of the third parameter that is also changed when the current value 705 of the first parameter is changed.

As described above, a method and apparatus for outputting parameter information for use in medical image scanning according to an exemplary embodiment enable a user to easily edit a predetermined parameter when the predetermined parameter and its associated parameters exist. In detail, a value range of the predetermined parameter that enables its associated parameter to be also changed when the predetermined parameter is change may be easily recognized, and thus unintended parameter changes may not occur.

In addition, a change value of the associated parameter when the predetermined parameter is changed may be easily recognized, and thus a user is able to recognize even the values of the associated parameters when editing the predetermined parameter.

Further, when a plurality of associated parameters exist, change values thereof are provided in stages, and thus a user may easily ascertain relationships among the associated parameters. Moreover, a limit value to which a predetermined parameter may be changed and the cause of the limit value are provided together, and thus a user may easily perform a parameter change for obtaining a desired image.

In addition, the exemplary embodiments may also be implemented through computer-readable code and/or instructions on a medium, e.g., a computer-readable medium, to control at least one processing element to implement any above-described embodiments. The medium may correspond to any medium or media that may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A method of outputting information of parameters for magnetic resonance imaging (MRI), the method comprising:
    outputting a bar comprising:
        a first change conflict region representing a first range of a first parameter, the first range enabling a second value of a second parameter to be changed together with a first value of the first parameter, the first range not enabling a third value of a third parameter to be changed, and the second parameter and the third parameter being associated with but different than the first parameter;
        a second change conflict region representing a second range of the first parameter, the second range enabling the second value of the second parameter and the third value of the third parameter to be changed together with the first value of the first parameter, the second range being separate from the first range, and the second change conflict region being separate from the first change conflict region;
        a limit region representing a third range to which the first parameter is not changeable, the third range being separate from the first range and the second range, and the limit region being separate from the first change conflict region and the second change conflict region; and
        a general region representing a fourth range of the first parameter, the fourth range not enabling any value of any parameter that is associated with but different than the first parameter to be changed together with the first value of the first parameter, the fourth range being completely outside the first range, the second range, and the third range, and the general region being separate from the first change conflict region, the second change conflict region and the limit region;
    receiving an input to the first change conflict region, the input corresponding to a fourth value of the first parameter in the first range;
    based on the input to the first change conflict region being received, outputting a fifth value to which the second parameter is changeable, according to the fourth value of the first parameter;
    receiving an input to the second change conflict region, the input corresponding to a sixth value of the first parameter in the second range;
    based on the input to the second change conflict region being received, outputting a seventh value to which the second parameter is changeable, along with an eight value to which the third parameter is changeable, according to the sixth value of the first parameter;
    receiving an input to the limit region without changing the first value of the first parameter, the input corresponding to a ninth value of the first parameter between a minimum value of the third range and a maximum value of the third range; and
    based on the input to the limit region being received, outputting a tenth value of a fourth parameter that is associated with but different than the first parameter and that causes the third range, without changing the first value of the first parameter.

2. The method of claim 1, wherein the outputting of the bar comprises outputting a maximum value of the first range and a minimum value of the first range.

3. The method of claim 1, wherein the input to the first change conflict region is received based on a cursor being positioned at the first change conflict region, and
    the cursor comprises any one or any combination of a keyboard cursor and a mouse cursor.

4. A non-transitory computer-readable storage medium storing a program comprising instructions to cause a computer to perform the method of claim 1.

5. An apparatus for outputting information of parameters for magnetic resonance imaging (MRI), the apparatus comprising:
an output interface; and
a processor configured to control the output interface to:
output a bar comprising:
a first change conflict region representing a first range of a first parameter, the first range enabling a second value of a second parameter to be changed together with a first value of the first parameter, the first range not enabling a third value of a third parameter to be changed, and the second parameter and the third parameter being associated with but different than the first parameter;
a second change conflict region representing a second range of the first parameter, the second range enabling the second value of the second parameter and the third value of the third parameter to be changed together with the first value of the first parameter, the second range being separate from the first range, and the second change conflict region being separate from the first change conflict region;
a limit region representing a third range to which the first parameter is not changeable, the third range being separate from the first range and the second range, and the limit region being separate from the first change conflict region and the second change conflict region; and
a general region representing a fourth range of the first parameter, the fourth range not enabling any value of any parameter that is associated with but different than the first parameter to be changed together with the first value of the first parameter, the fourth range being completely outside the first range, the second range, and the third range, and the general region being separate from the first change conflict region, the second change conflict region and the limit region;
receive an input to the first change conflict region, the input corresponding to a fourth value of the first parameter in the first range;
based on the input to the first change conflict region being received, output a fifth value to which the second parameter is changeable, according to the fourth value of the first parameter;
receive an input to the second change conflict region, the input corresponding to a sixth value of the first parameter in the second range;
based on the input to the second change conflict region being received, output a seventh value to which the second parameter is changeable, along with an eight value to which the third parameter is changeable, according to the sixth value of the first parameter;
receive an input to the limit region without changing the first value of the first parameter, the input corresponding to a ninth value of the first parameter between a minimum value of the third range and a maximum value of the third range; and
based on the input to the limit region being received, output a tenth value of a fourth parameter that is associated with but different than the first parameter and that causes the third range, without changing the first value of the first parameter.

6. The apparatus of claim 5, wherein the processor is further configured to control the output interface to output a maximum value of the first range and a minimum value of the first range.

7. The apparatus of claim 5, wherein the processor is further configured to control the output interface to output a maximum value of the second range and a minimum value of the second range.

8. The apparatus of claim 5, wherein the tenth value of the fourth parameter is used to change the third range.

9. The apparatus of claim 5, wherein the input to the first change conflict region is received based on a cursor being positioned at the first change conflict region, and
the cursor comprises any one or any combination of a keyboard cursor and a mouse cursor.

* * * * *